(12) United States Patent
Leiper (10) Patent No.: US 7,438,233 B2
(45) Date of Patent: Oct. 21, 2008

(54) BLINDED ELECTRONIC MEDICAL RECORDS

(75) Inventor: Thomas W. Leiper, Stamford, CT (US)

(73) Assignee: Shepherd Medical Solutions LLC, Canton, NC (US)

( * ) Notice: Subject to any disclaimer, the term of this patent is extended or adjusted under 35 U.S.C. 154(b) by 301 days.

(21) Appl. No.: 11/321,102

(22) Filed: Dec. 29, 2005

(65) Prior Publication Data

US 2006/0163340 A1 Jul. 27, 2006

Related U.S. Application Data

(60) Provisional application No. 60/671,162, filed on Apr. 14, 2005, provisional application No. 60/646,832, filed on Jan. 24, 2005, provisional application No. 60/646,833, filed on Jan. 24, 2005, provisional application No. 60/646,838, filed on Jan. 24, 2005.

(51) Int. Cl.
*G06K 19/00* (2006.01)
(52) U.S. Cl. ............... 235/487; 235/375; 705/2; 705/3; 705/54
(58) Field of Classification Search ........... 235/487, 235/375; 705/2, 3, 54; 707/9
See application file for complete search history.

(56) References Cited

U.S. PATENT DOCUMENTS

| 2004/0078238 A1 | 4/2004 | Thomas et al. ............... 705/3 |
| 2004/0107210 A1 | 6/2004 | Yang et al. ............. 707/104.1 |
| 2004/0117215 A1* | 6/2004 | Marchosky ................. 705/3 |
| 2005/0021519 A1* | 1/2005 | Ghouri ..................... 707/9 |
| 2005/0197860 A1* | 9/2005 | Joffe et al. ................ 705/2 |
| 2005/0234745 A1* | 10/2005 | Schoenberg ............... 705/3 |
| 2005/0267782 A1* | 12/2005 | Zahlmann et al. .......... 705/3 |

* cited by examiner

*Primary Examiner*—Michael G. Lee
*Assistant Examiner*—Kristy A Haupt
(74) *Attorney, Agent, or Firm*—St. Onge Steward Johnston & Reens LLC (57) ABSTRACT

A system for transferring and updating sensitive data including at least one consolidator including a plurality of sensitive data records, a transaction processor for processing a transfer of data from one or more of the sensitive data records; software executing on the transaction processor for receiving a data request from a requester, software executing on the transaction processor for determining the at least one consolidator having the data, and software executing on the transaction processor for introducing the requester to the at least one consolidator, wherein the at least one consolidator transfers the data omitting data identifying the particular member.

32 Claims, 8 Drawing Sheets

BLINDED ELECTRONIC MEDICAL RECORDS

CROSS-REFERENCE TO RELATED APPLICATIONS

This application claims priority benefits under 35 § U.S.C. 119(e) of the U.S. Provisional Application No. 60/646,832, filed on Jan. 24, 2005, U.S. Provisional Application No. 60/646,833, filed on Jan. 24, 2005, U.S. Provisional Application No. 60/646,838, filed on Jan. 24, 2005, and U.S. Provisional Application No. 60/671,162, filed on Apr. 14, 2005, the disclosures of all of which are herein incorporated by reference.

FIELD OF THE INVENTION

The invention relates to the electronic record keeping systems, and more specifically to a system and method for the storage and distribution of sensitive data such as electronic medical records.

BACKGROUND OF THE INVENTION

Some integrated software systems for keeping sensitive records electronically have been developed and are in use, for example, by medical facilities for the storage of electronic medical records ("EMR"). These medical records, however, are often localized to the particular treating doctor or facility. For example, a patient may have a separate and unique medical record at each and every doctor's office and/or medical facility that she has visited. Therefore, each doctor generally does not have access to a patient's complete medical history when providing a diagnosis or a new treatment. This can often hinder a doctor's ability to select the best treatment for a patient.

Patient's medical records also contain a wealth of information useful for the research community. For example, each medical record generally contains detailed information such as symptoms of particular illnesses and the effectiveness of treatments which may not otherwise be accessible to physicians or researchers. Having blind access to such information could be invaluable in the search for new treatments and cures for many illnesses. Further, access to such data would provide physicians with an abundance real life data for use in evaluating treatment options for their patients.

A significant problem in the accessibility of medical records is the difficulty of synchronizing and updating the various instances of the patient's medical records. More important, however, are the security issues associated with sharing medical records. Most patients would likely be hesitant to make their records accessible, for treatment or otherwise, without being sure that the data is secure from unauthorized access and identification. Most patients would likely prefer to have complete control over authorizing who is permitted access. Other factors complicating the sharing or release of a patient's medical records include the regulatory requirements imposed by the Health Insurance Portability and Accountability Act of 1996 ("HIPAA"). This regulatory framework, established by Congress, obligates physicians to maintain the confidentiality of patient records that identify particular individuals and any medical conditions they may suffer from.

It is therefore desired to provide a system and method for transferring, maintaining and updating sensitive data, such as electronic medical or health records. It is further desired to provide a means of blinding medical records to allow for the clinical use of anonymous medical information, such as for blinded research queries.

SUMMARY OF THE INVENTION

According, it is an object of the present invention to provide a global system of maintaining sensitive records, a blinded record format, and a transport medium for sending and receiving sensitive information such as medical records. It is a further object to provide a means for reliably and securely using such records for the reconstruction of identifiable patient records for the purposes of treatment and for the merchandising of research data.

It is a further object to ensure that the sensitive data and identifying information therein is absolutely secure by way of third party validation methods, blinding of data, and ensuring that the replication of sensitive data is minimized. It is a further object to provide an audit means to police accesses of sensitive data and to also flag and prevent suspicious activity or errors in record reconstruction.

These and other objectives are achieved by providing a system for transferring and updating sensitive data, including one or more consolidators having access to a plurality of sensitive data records, at least some of the data records including data identifying one or more particular members, a transaction processor for processing a transfer of data from one or more of the sensitive data records, software executing on the transaction processor for receiving a data request from a requester, software executing on said transaction processor for determining at least one consolidator having access to the requested data, and software executing on said transaction processor for introducing the requester to the at least one consolidator, wherein the requestor receives at least a portion of the requested data, the portion excluding data identifying the one or more particular members. In some embodiments, the plurality of sensitive data records include at least some first data fields including anonymous data and at least some second data fields including non-disclosable data identifying at least one particular member.

Further provided is a system for transferring and updating sensitive data, including at least one data agent having access to a plurality of sensitive data records, a transaction processor for processing a transfer of data from one or more of the sensitive data records, software executing on the transaction processor for receiving a data request from a requester, software executing on the transaction processor for determining the at least one data agent having access to the data, software executing on the transaction processor for transmitting a transaction request to the at least one data agent, and software executing on the transaction processor for receiving blinded data responsive to the data request from the at least one data agent and transmitting the blinded data to the requester. The system may further include software executing on the transaction processor for determining a cost of the transaction.

DETAILED DESCRIPTION OF THE DRAWINGS

Figure 1:
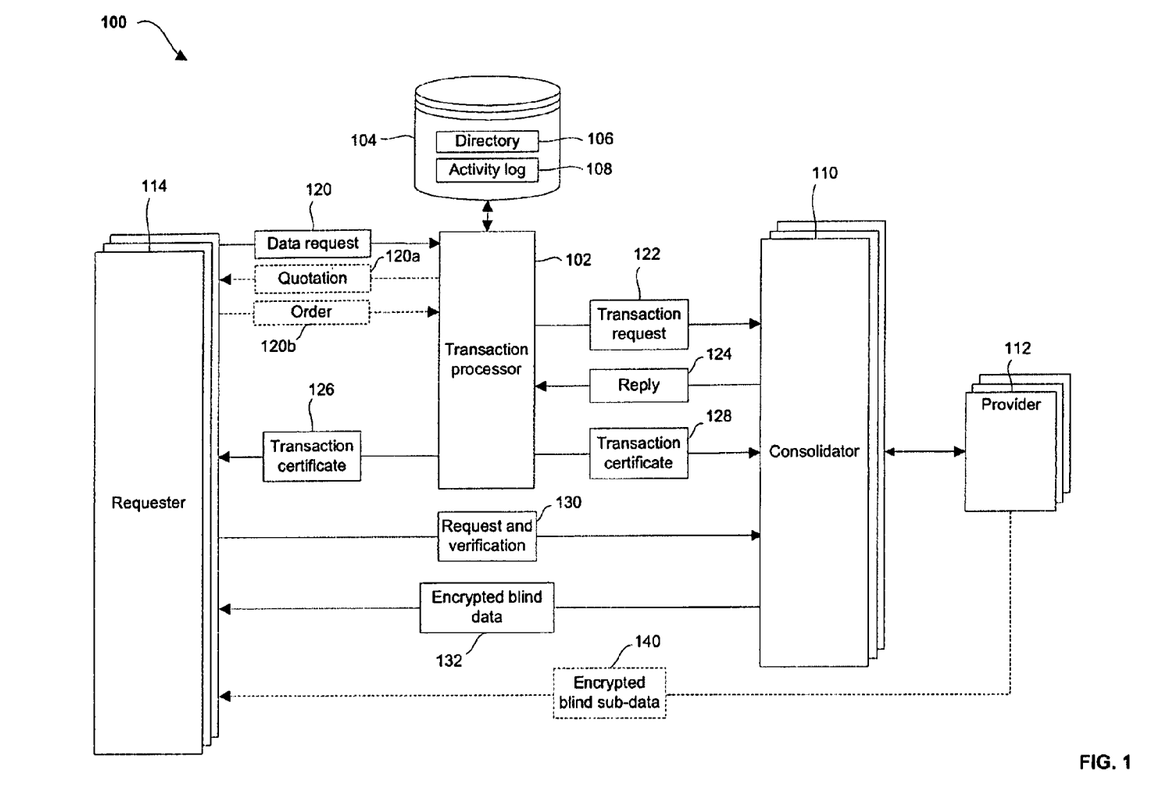
FIG. 1 is a schematic view of a system for transferring and updating sensitive data according to the present invention.

FIG. 1 shows a system 100 for maintaining and transferring sensitive data according to the present invention. The system 100 includes a transaction processor 102. The transaction processor 102 may be any processor, controller or server for executing one or more software applications. The transaction processor 102 may be in communication with one or more databases 104 or storage means including any number of data records. The transaction processor 102 and database 104 may be co-located or remote to one another, e.g., accessible via a communications network.

The database 104 may include a directory 106. The directory 106 may include, e.g., a directory of member ID's corresponding to members or users of the system 100 and/or a directory of consolidators (e.g., consolidator ID's) accessible by the transaction processor 102. In some embodiments, the directory 106 may further include a directory of data types and corresponding locations (e.g., consolidators) where the data types may be found. For example, the directory 106 may include directories of the best locations (e.g., locations have the most of the data type, fastest access, most reliable, etc.) to find particular types of data. The directory 106 may also include a directory of authorized and/or verified requesters.

As shown in FIG. 1, the database 104 also includes an activity log 108, e.g., for logging all transactions performed or attempted by the transaction processor 102. The activity log 108 therefore provides a means of auditing substantially all the activity of the system 100. Still further, the database 104 may include transaction rules, stored results from previous data requests and/or stored searches strings performed by the transaction processor 102.

Further included in the system 100 is at least one consolidator 110 or data aggregator. The consolidator 110 may be a device, entity, or person having access, authority, and/or control over any number of sensitive data records. For example, the consolidator 110 may be an individual (e.g., accessing the system 100 via a user interface) having the exclusive control over his or her own medical records or it may be an individual's doctor's office. In one preferred embodiment, the consolidator 110 is an entity (or processor or server thereof) having the exclusive authority to aggregate and control access to a plurality of sensitive data or data records but not the ability to alter the data contained in the records (other than such refinements necessary to create a database of consolidated records).

In another embodiment, the consolidator 110 may an entity providing members the service of maintaining and controlling access to the sensitive records such as financial or medical records. The consolidator 110 may be supported by fees charged to each member and/or advertising to the members. For example, the consolidator 110 may sell advertising on a web/user interface of the consolidator 110 accessible by the members.

As noted, the present invention contemplates the situation where (1) the consolidator 110 operates a network server where member data is stored, or (2) the member's data is stored locally in individual computers accessed by the consolidator 110 computer system. The sensitive records maintained or accessible by the consolidator 110 may include data consolidated from any number of data providers 112 or points of entry. The providers 112 or points of entry may include, for example, a doctor, a doctor's office, hospital, or health care facility. The consolidator 110 may therefore be a single source for receiving and maintaining all data generated about a particular member by all the points of entry and/or providers 112. Alternatively, the consolidator may not have any copies of the patient data under its control, but only have a meta-index to locate patient data located in multiple locations (such as individual physician offices) and certain rights to access, select, compile, and/or reproduce selected portions of patient data records.

Figure 2:
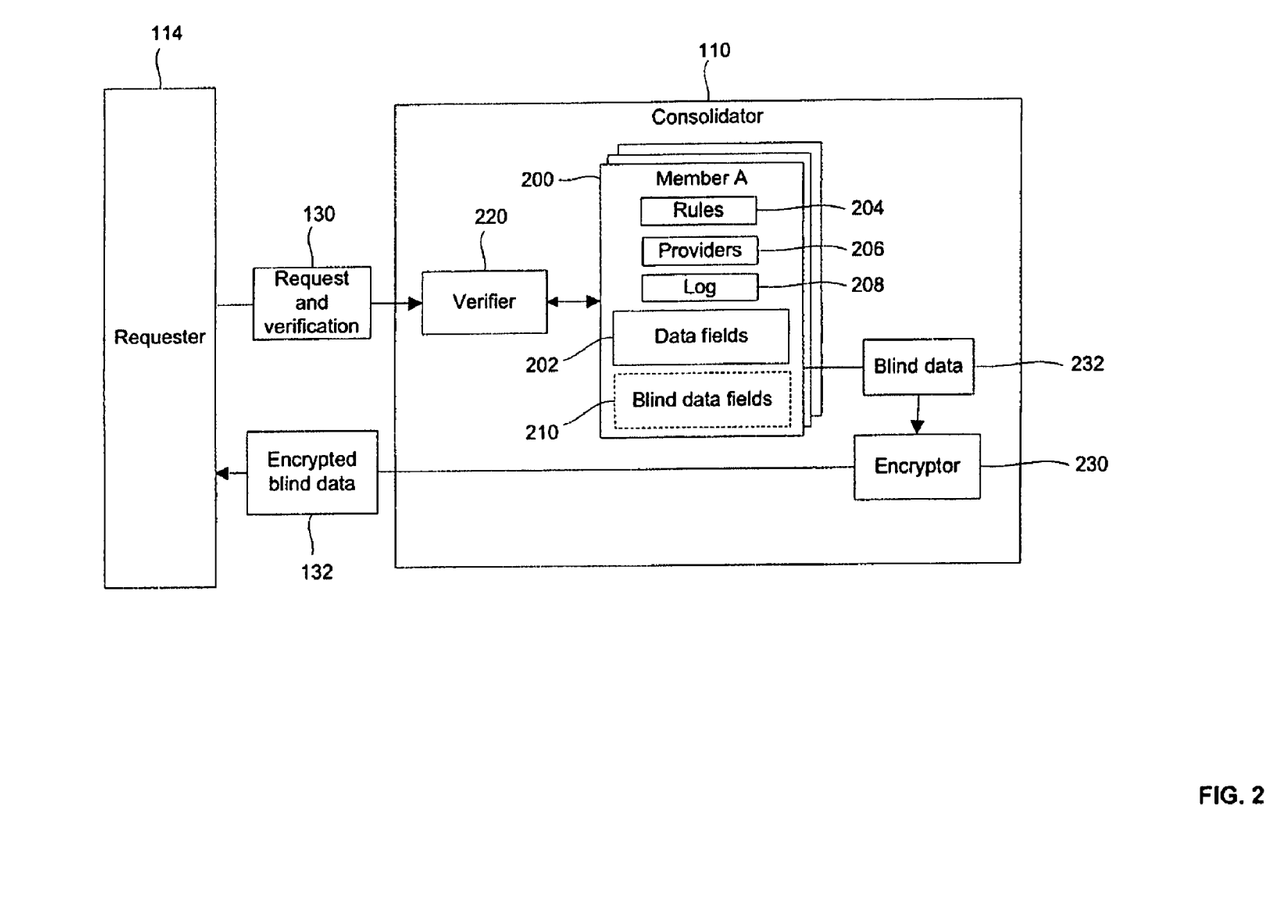
FIG. 2 is an exploded view of a consolidator of data according to the system shown in FIG. 1.

As shown in FIG. 2, the consolidator 110 may, for example, maintain or otherwise have access to a data record 200 for a particular member A. The data record 200 may include any number of data fields 202 for storing sensitive data (e.g., medical data) and/or non-disclosable data (e.g., HIPAA protected data). For example, the data record 200 and/or data fields 202 may include member A's entire medical history. The term "medical history" as used herein means any and all medical information or data generated about a particular patient by all providers and/or points of entry. Therefore, the medical history may include all notes and observations taken during office visits, lab test results, diagnosis's, prescribed medications, and any data provided to the medical history by the particular patient. The data record 200 may be updated by each provider 112 as new data is generated, at a specific time interval, or at the request of the consolidator 110. It should be noted that, in some embodiments, the data fields 202 may only temporarily store data. For example, the data fields 202 may only be populated with data acquired from any number of providers of data in furtherance of a transaction. In some other embodiments, the data record 200 may include indicators of the types of data available for the member A and the locations thereof.

The data record 200 may further include rules 204 pertaining to the access of the sensitive data. The rules 204 may include any number of restrictions and/or requirements regarding the release of member A's data. The rules 204 may be created by the member A, a doctor or health care facility providing data to the data record 200, and/or the consolidator 110 (or an administrator thereof). Important to the present invention is that members preferably have complete control over their data. Therefore, the member A may determine whether to provide access to any data of the data record 200 and to what extent, when and to whom data may be transferred, and/or any other desired preferences. Such preferences may, for example, be indicated or modified via a member portal or user interface to the system 100 or the particular consolidator 110 of the member A's data.

The data record 200 may further include a table or record of providers 206 (e.g., authorized providers of data). For example, the table of providers 206 may include reference to each provider 112 having contributed data to the data record 200, each provider 112 approved for access (restricted or otherwise) to the data record 200, or any providers 112 identified (or excluded) by the member 200. The data record 200 may also include a log 208, e.g., for recording each instance of data entry or retrieval to/from the data record 200 or aggregation of data pertaining to member A.

Referring back to FIG. 1, the system 100 includes any number of requesters such as requester 114. The requester 114 may, for example, be a hospital or other health care provider requesting data regarding a particular patient to facilitate the treatment of that patient. For example, any provider 112 may also be a requester 114. The requester 114 may also be a researcher seeking blind or anonymous data relating to a particular illness and/or treatment. The researcher may be, for example, an illness research facility, a university or a doctor (or patient) seeking comparative analysis data to aid in the treatment of a particular patient. The research may seek blind case studies on particular patients meeting a search criteria and/or statistical or summary data on a population of such patients. Therefore, the system 100 preferably allows any number of research search criteria and variables such as illnesses, treatments, demographics, environment, age, sex, weight, etc. As one of ordinary skill in the art will understand upon reading the remainder of the description, the present invention therefore allows researchers to instantaneously access a wealth of medical information, using a targeted search criteria (e.g., via a web interface), that may otherwise take months or years to acquire through clinical trials.

As shown in FIG. 1, the requester 114 may submit a data request 120 to the transaction processor 102. The data request 120 may, for example, be submitted via a communications network such as the Internet. As discussed above, the data request 120 may be a request for all or a portion of data regarding a particular patient or member, i.e., a patient data request. For example, a hospital may request data regarding a patient having no prior relationship (or medical history) with the hospital, such as a new patient arriving due to an emergency. Such a data request 120 may for general data regarding the patient, or for specific data, such as a request for data regarding the patient's current prescriptions or drug allergies.

As one of ordinary skill in the art will understand, a data request 120 for data relating to a particular patient will require means to ensure that the requestor 114 has authority to make the request. For example, the system 100 may require that such a data request 120 include a valid member ID of the patient and any number of other identifiers. In some embodiments, the requestor 114 will be required to include a valid and authorized requester ID, the member ID of the particular patient, and/or a consolidator ID of the consolidator 110 having the requested data.

The data request 120 may alternatively be a request for the retrieval of blind research data. The blind research data may include blind data assembled from a plurality of patients or members whose data is accessible by the transaction processor 102. It should be noted that any data request 120 may be a request for a single transmission of available data or a request for continuous data (e.g., as responsive data becomes available).

The data request 120 is received by the transaction processor 102. The transaction processor 102 may then query the database 104 (e.g., the directory 106) to determine whether any data may be available for the data request 120. The transaction processor 102 may, in addition or in combination, directly query one or more consolidators (e.g., 110), or substantially all of the consolidators, to determine if any data is available. In some embodiments, the transaction processor 102 further verifies the requester 114.

In some embodiments, particularly those related to research inquiries, the transaction processor 102 may optionally respond to the requester 114 with a quotation 120a (e.g., price and/or rate). For example, the transaction processor 102 may determine the number of consolidators 110 having relevant data and/or the quantity of available data and provide a dollar value for the data request 120 based on the determinations. It is contemplated that predetermined dollar values or rates may be assigned to particular data types and particular quantities of data to be transmitted. The quotation 102a may further include suggested modifications to the data request 120 and/or prepackaged or stored data requests that may be available. In response to the quotation 120a, the requester 114 may then transmit an order 120b. The order 120b may be an agreement to the quotation 120a and/or a modification (e.g., narrowing) of the data request 120.

If the transaction processor 102 determines that data is available from one or more particular consolidators (and the requester 114 transmits an order 120b if necessary), the transaction processor 102 may generate and transmit a transaction request 122 to the one or more consolidators (e.g., 110). For example, the transaction processor 102 may determine that the data request 120 relates to a member A whose data is maintained by consolidator 110. A transaction request 122, indicating that requester 114 has requested data regarding member A, is then transmitted to consolidator 110. The transaction request 122 may include a member ID (or other indicator of the member and/or type of data requested) and/or at least a portion of the data request 120. The transaction processor 102 may alternatively determine that a plurality of consolidators have data related to the data request. For example, the data request 120 may be a research query for all information related to the treatment of a particular illness using a specified drug. The transaction processor 102 may then transmit the transaction request 122 to each of the plurality of consolidators having the data.

Upon receiving the transaction request 122, the consolidator 110 may query data records pertaining to the transaction request 122 and/or data request 120. For example, the consolidator may query member A's data record 200 to determine whether to permit the transaction. The consolidator 110 may, in particular, query member A's rules 204 and providers 206. The consolidator 110 may further query any number of global rules pertaining to all members of the consolidator 110.

The consolidator 110 may then transmit a reply 124 to the transaction processor 102. The reply 124 may include an indication of the consolidator's consent to the transaction processor 102 to initiate the requested transaction or, in some instances, particular rules or requirements that must be met to initiate the transaction. The reply 124 may further include a description of the types and/or categories of data available regarding the transaction request 122.

Following receipt of the consolidator's reply 124, the transaction processor 102 generates and transmits a transaction certificate 126/128 to the requester 114 and consolidator 110. Each transaction certificate 126 and 128 contains information to enable a secure transaction between the requester 114 and consolidator 110. For example, the system 100 may employ a public key infrastructure and a transaction time limitation. The transaction certificate 126 may therefore include a public "lock" key of the consolidator 110 and a time at which to transmit a request to the consolidator 110. The transaction certificate 126 may further include a unique identifier assigned to the transaction. Likewise, the transaction certificate 128 may include the public key of the requester 114, the unique identifier, and the time in which a request will be received.

It should be noted that often the transaction processor 102 will know the public key of each the requester 114 and consolidator 110. For example, the system 100 may require each requester, provider and consolidator to register prior to using the system 100. Further, the transaction processor 102 may locate the public keys in either or both of the directory 106 and activity log 108. However, if the transaction processor 102 does not (e.g., if the requester 114 is a first time user of the system 100), the public key must be requested from the requester 114 and/or consolidator 110 prior to transmitting the transaction certificates 126/128.

As shown in FIG. 1, the requester 114 may next transmit a request and verification 130 directly to the consolidator 110. The request and verification 130 may include a description of the specific data requested as well as verification information including, e.g., the unique identifier and/or the requester's public key. As one of ordinary skill in the art will understand, if the request is not received in the given time, the transaction will expire. If the request is received in the appropriate time and the verification information is correct, the consolidator 110 may transmit data to the requester 114. As discussed more below, the consolidator 110 may, alternatively or in combination, generate sub-requests (or "child" transactions) to one or more providers 112 for the requested data. The sub-requests may occur prior to, during or after sending a portion of the requested data to the requestor 114.

As shown in FIG. 2, the consolidator 110 may assemble data from one or more data records 200 for transmission to the requester 114. Preferably the consolidator 110 assembles the data in the form of blind data 232. The blind data 232 may be, for example, data containing no indication of the patient or member to which it pertains and/or any disclosable data (e.g., not protected by HIPAA). The blind data 232 may also be referred to as case study data (e.g., with respect to research related data requests).

The blind data 232 may be assembled from blind data fields 210 of the data record 200. Such blind data fields 210 may contain substantially all of the data contained in the data fields 202 (e.g., member A's medical history) excluding, however, all non-disclosable data and/or all data otherwise indicating the identity of the member A. Such identifying information may include, for example, the member's name, social security number, address, telephone number, and/or any other information tending to identify the member A. In some embodiments, the blind data fields 210 may be temporary data fields and contain only data related to the specific data request 120 and/or request and verification 130. For example, the blind data and/or blind data fields 210 may be created upon receipt of a data request 120 and/or request and verification 130. Therefore, separate blind data fields 210 need not be permanently maintained.

It should be noted that the consolidators 110 according to the present invention shall include security measures to ensure that non-disclosable data is not included in the blind data fields 210 or transmitted as blind data 232 to a requester. For example, the consolidator 110 may include software that periodically screens the blind data fields 210 to locate and remove non-disclosable data (e.g., a name, address, etc). Further, the consolidator 110 may include a filter to actively remove any identifying and/or non-disclosable data prior to transmitting a response to a data request.

For temporary identification purposes, the blind data 232 is generally assigned an instance ID pertaining to the particular transaction. The blind data 232 (e.g., blind requested data) is then encrypted by the consolidator 110. For example, the blind data 232 may be encrypted by an encryptor 230 of the consolidator 110. The encryptor 230 may be embodied in software, hardware or a combination thereof. As discussed above, the encryptor 230 may encrypt the data in a manner which requires the requester 114's private "unlock" key, known only to the requester 114, to decrypt. As one of ordinary skill in the art will understand, however, any known method of data encryption may be used by the encryptor 230 to generate encrypted blind data 132. The encrypted blind data 132 may then be transmitted to the requester 114.

In some situations, particular portions of blinded data 232 may also be assigned a blinding code. For example, in situations where a portion of the non-disclosable data is needed by the requester, such as when a hospital request requires (and has been granted permission) the address of patient, those particular portions may be replaced with a blinding code. The blinding code may, for example, be a randomly generated number. The non-disclosable data corresponding to the blinding code may then be separately transmitted to the request 114 for inserting in place of the blinding code.

Upon receipt by the requester 114, the encrypted blind data 132 may be decrypted. Further, the decrypted blind data may, in some instances, be re-associated with the particular member to which it pertains. For example, for a requester 114 (e.g., a doctor or hospital) having requested data pertaining to a particular member, the transaction certificate 126 (and/or 128) will contain sufficient information to allow the requester 114 to re-associate the blind data with the particular member. The requester 114 will have the identifying information in advance, or it may be supplied in the transaction certificate. However, for a requester 114 (e.g., researcher) having only requested blinded data related to any number of members, the blinded data and/or transaction certificate will provide no means to identify the particular member to which it pertains.

Either or both the requester 114 and/or consolidator 110 may transmit a confirmation to the transaction processor 102 when the transaction is complete. The transaction processor 102 may then generate a log of the transaction in the activity log 108. If a confirmation is not received or the transaction is otherwise not completed, the transaction processor 102 may likewise generate a log of the attempted transaction.

Figure 3:
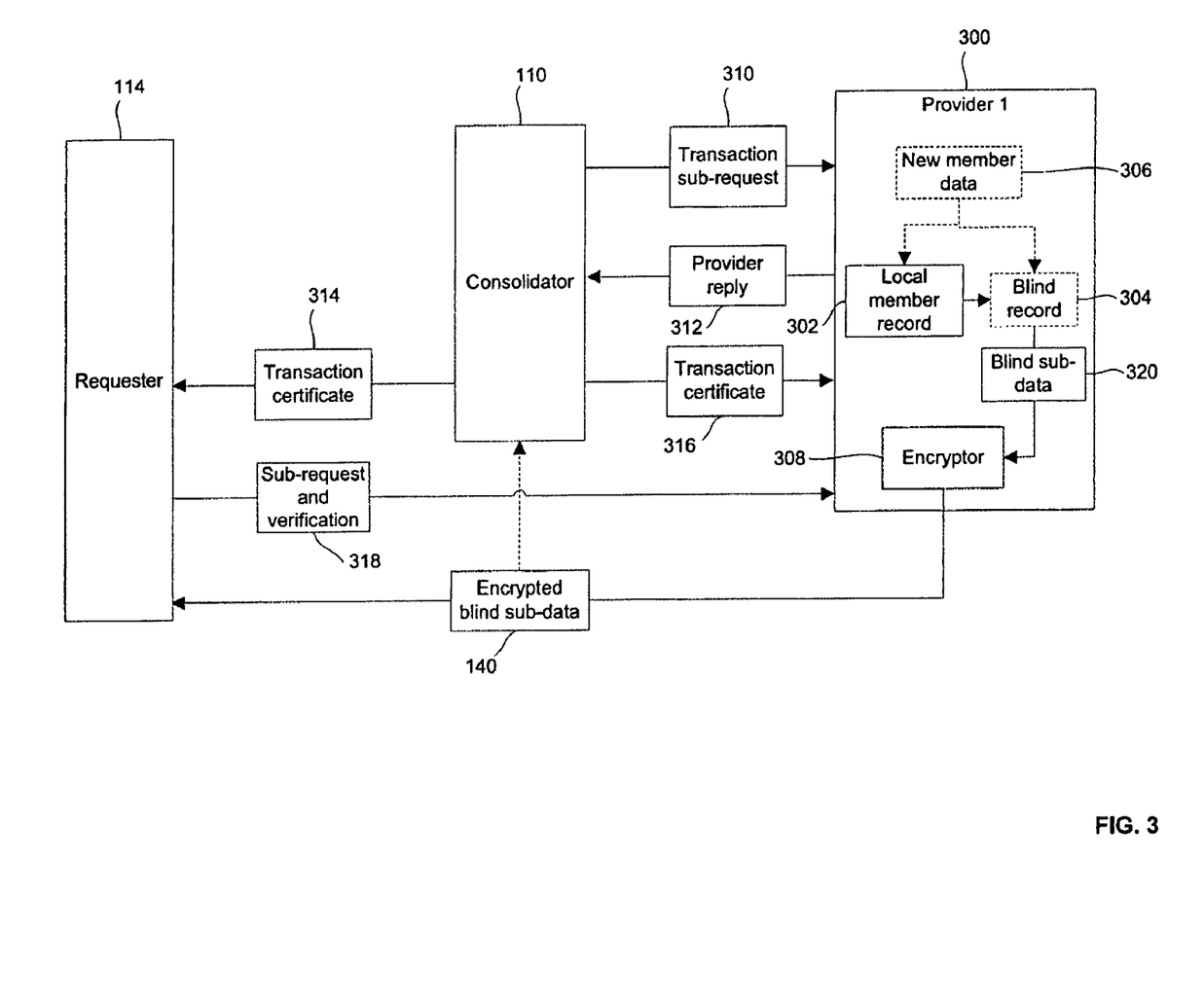
FIG. 3 is an exploded view of a provider of data according to the system shown in FIG. 1.

FIG. 3 shows an exploded view of a provider 300 of the system 100. Each provider 300 (or 112) or "point of entry" generally stores or otherwise maintains a local member record 302 for each particular member or patient of the provider 300. For example, the local member record 302 may be a patient medical record created and/or maintained by the provider 300 (e.g., a treating doctor or hospital). Preferably the local member records of each provider exist in a common format to better enable the exchange of data via the system 100. The local member record 302 may include any and/or all data generated by the provider 300 regarding the particular member. Further, the local member record 302 may also include data generated by other providers and subsequently validated by the provider 300 (as discussed more below).

Some providers 300 may further store and/or maintain a blind record 304 for at least some members. The blind record 304 may include at least a portion of the data of the local member record 302, however, with all non-disclosable and/or data identifying the member removed. However, many other providers may simply generate the blind record 304 (e.g., a temporary blind record) when necessary for transactions. The local member record 302 and/or blind record 304 may further be updated by the provider 300 (e.g., in real time) as new member data 306 is generated, received and/or validated by the provider 300.

FIG. 3 further shows a means by which the consolidator 110 may request data (e.g., sub-data) from the provider 300. The consolidator 110 may, for example, request data from any number of providers 300 following a data request 120 from a requester 114. As described above, some consolidators 110 may not store a substantial amount of data locally and therefore will request data from the providers 300 upon each request from a requestor 114. For example, some members may prefer that their data (e.g., medical history) is maintained only by individual providers and not stored by a consolidator 110. Each particular data request will therefore require a collection and consolidation of the requested data. Some other consolidators 110 may store some or all data, but may request additional data when a data record 200 is not up to date or additional data and/or clarification is needed from the provider 300.

A sub-request from the consolidator 110 to a provider 300 may operate in a similar manner to that of a data request 120 to the consolidator 110. As shown, the consolidator 110 may transmit a transaction sub-request 310 to the provider 300. The transaction sub-request 310 may indicate that requester 114 has requested data regarding a particular patient of provider 300 (e.g., member A). Alternatively, the transaction sub-request 310 may indicate that requester 114 (e.g., researcher) is seeking any and all blind data relating to a particular illness.

Upon receiving the transaction sub-request 310, the provider 300 may query any number of local member records (e.g., 302) to find data pertaining to the transaction sub-request 310 and/or data request 120. As one of ordinary skill in the art will understand, the provider 300 may also query any number of rules to determine whether to permit the transaction. If responsive data is located and the transaction is permitted, the provider 300 may transmit a provider reply 312 to the consolidator 110.

The consolidator 110 then generates and transmits a transaction certificate 314/316 to both the requester 114 and provider 300. The transaction certificate 314/316 may include, for example, a unique identifier of the transaction, public keys of the requester 114 and provider 300, and transaction time limit. The requester 114 may then transmit a sub-request and verification 318 to the provider 300. If the sub-request 318 is received in the appropriate time and the verification information is correct, the provider 300 may transmit data to the requester 114.

As shown, the provider 300 first assembles blind sub-data 320 for transmission to the requester 114. If the provider 300 does not maintain a blind record 304, the blind sub-data 320 is retrieved from one or more local member records 302 and the non-disclosable or identifying information is removed. The blind sub-data 320 is then encrypted (e.g., via an encryptor 308) and encrypted blind sub-data 322 transmitted to the requester 114 (and/or consolidator 110). Further either or both the requester 114 and provider 300 may transmit a confirmation or log to the consolidator 110.

Figure 4:
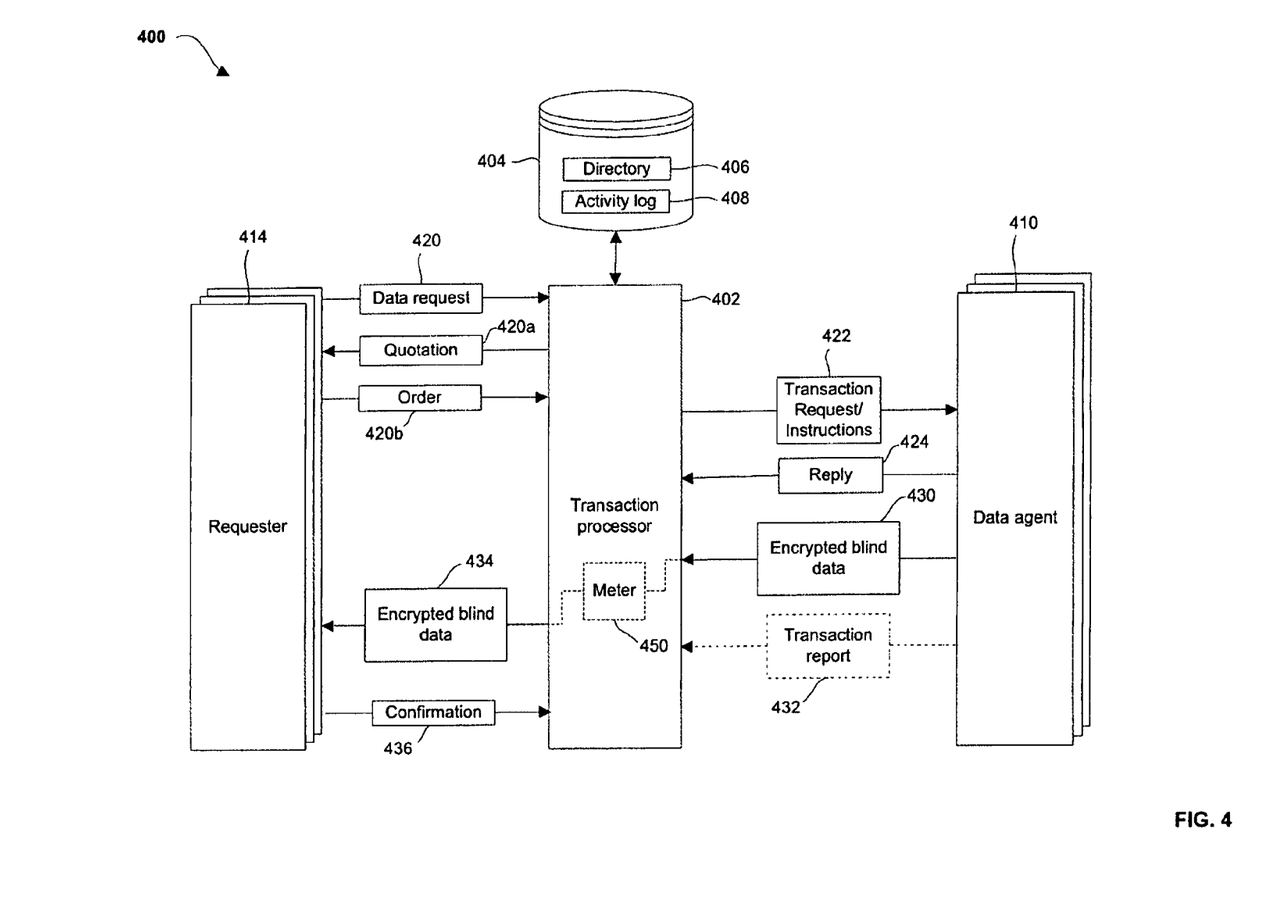
FIG. 4 is a schematic view of another embodiment of the system for transferring and updating sensitive data according to the present invention.

FIG. 4 shows another embodiment of a system 400 according to the present invention. The system 400 includes a transaction processor 402 (e.g., or 102) and a database 404. As in the database 104 described above, the database 404 may include a directory 406 and an activity log 408. The database 404 may further include transaction rules and/or data for determining transaction quotations. The system 400 may further include any number of data agents 410. The data agent 410 may, for example, be a consolidator. However, the data agent 410 may be a data source agent having access to or the ability to query any number of data sources. Some data agents may, for example, provide access to particular types of data or data in particular regions or locations.

The transaction processor 402 may receive a data request 420 (e.g., data inquiry or request for quote) from a requester 414. The requester 414 may be a provider. However, in the present embodiment, the requester 414 is more preferably a researcher. Upon receiving the data request 420, the transaction processor 402 may query the database 404 and/or particular data agents 410 to verify and/or approve the requester 414 and data request 420. For example, the transaction processor 402 may consider transaction rules in the database 404. The rules may include, e.g., limitations on the size of the data pool requested (minimums and maximums), limitations on the amount of data transferred per day, restrictions on repetitive data requests or extremely narrow searches (e.g., likely to be attempts to identify particular members), restrictions on data requests attempting to evaluate a particular provider's performance, etc. The transaction processor 402 may further determine data availability for quotation purposes. For example, the transaction processor 402 may determine (or estimate) the quantity and types of available data that is responsive to the data request 420.

The transaction processor 402 may then transmit a quotation 420a or cost estimate of the requested data to the requester 414. The quotation 420a may be a total transaction cost estimate or a rate (or series of rates) to be used to later compute a total transaction cost. The quotation 420a may further provide details of the available data on which the quotation 420a is based. As discussed above, the transaction processor 402 may (e.g., via the quotation 420a) suggest any number of prepackaged or recently completed data requests, e.g., that may be available at a lesser cost. The requester 414 may then transmit an order 420b to the transaction processor 402. As described above, the order 420b may an agreement to the quotation 420a and/or a modification of the data request 420.

To initiate the retrieval of the requested data, the transaction processor 402 may transmit a transaction request or instructions 422 to one or more data agents 410. The data agent 410 may reply if necessary to indicate consent or lack thereof to the requested transaction. For example, a data agent or particular member whose blind data may be retrieved in the search may indicate (e.g., via a predefined rule, etc) not to provide some data to the requester 414. The data agent 410 may then assemble data (e.g., blind data) for transmission to the transaction processor 402. In some embodiments, the data agent 410 may subsequently transmit the transaction instructions 422 to any number of other data agents having access to data responsive to the data request 420. Any one or all of the data agents (e.g., 410) may then transmit encrypted blind data 430 to the transaction processor 402.

As shown, the transaction processor 402 in the present embodiment generally receives the encrypted blind data 430 rather than being transmitted directly to the requester 414. This embodiment may be desirable, e.g., for research data requests/inquiries wherein it may be preferred for the requester to communicate only with the transaction processor 402 and to not learn the identity of the consolidators, providers and/or data agents. As one of ordinary skill in the art will understand, however, either the transaction processor 102 or the transaction processor 402 may perform the either one or both of the transactions shown in FIGS. 1 and 2.

Next, the data agents may optionally transmit a transaction report 432 to the transaction processor 402. The transaction report 432 may, for example, provide information for determining the cost of the transaction. Alternatively, or in combination, the transaction processor may employ a meter 450 to gather information for determining transaction costs. The meter 450 may quantify the amount of data received from the data agent 410 and/or transmitted to the requester 414. The meter 450 may further measure any other parameters related to the data. The requester 414's cost and/or future cost quotations may be based on the meter 450. For example, the meter 450 may measure the time to complete the transaction, the time of day (e.g., peak or off-peak), the volume of data and/or number of data fields transmitted, the data size (e.g., kilobytes), or any other measurable data parameter. The transaction processor 402 may next transmit encrypted blind data 434 to the requester 414 and receive a confirmation 436.

Figure 5:
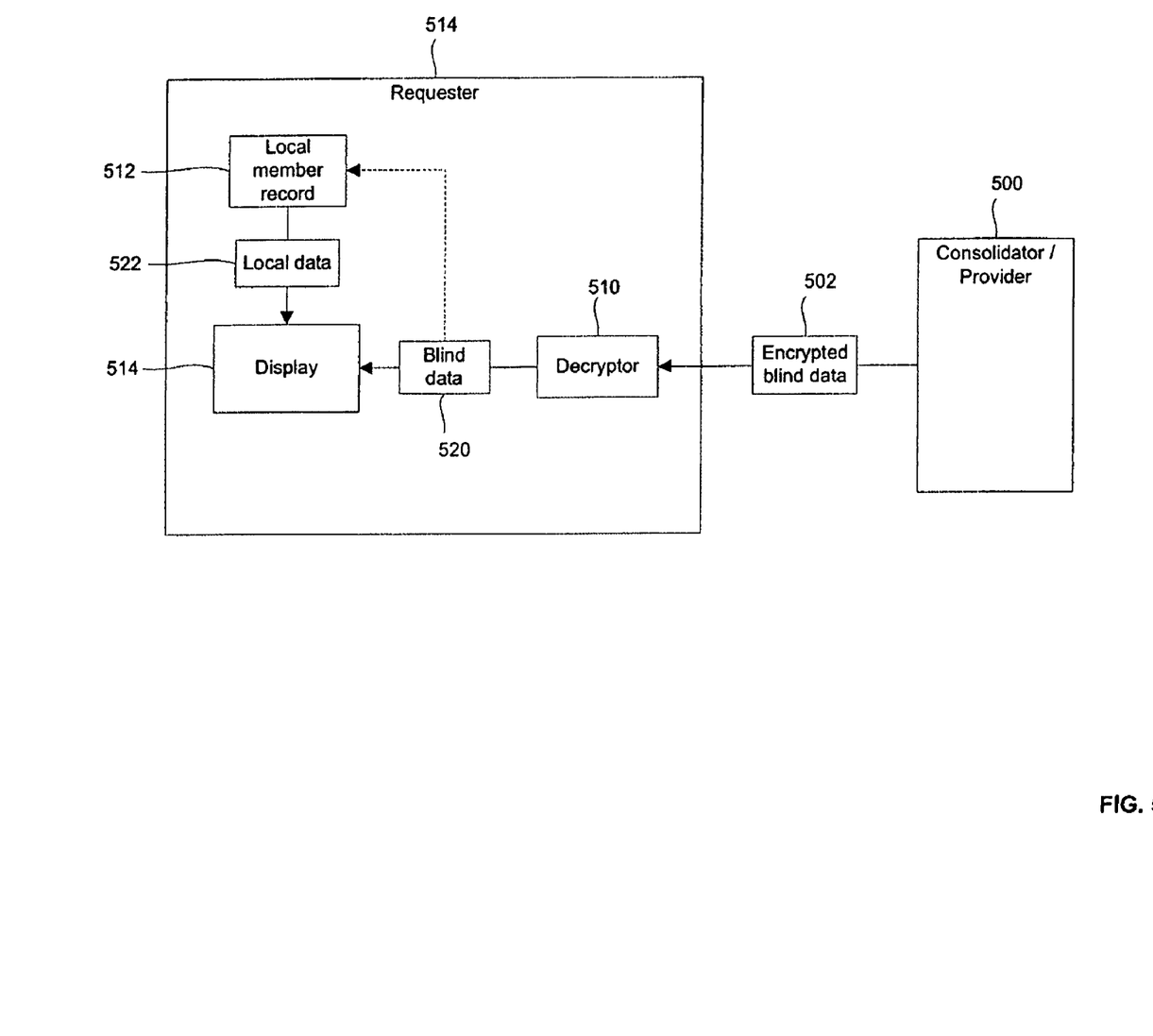
FIG. 5 is a schematic view of a requestor of data according to the systems shown in FIGS. 1-4.

FIG. 5 shows an exploded view of a requester (e.g., 114 or 414) according to the present invention. As discussed above, the requester 114 may be a provider, a researcher or any other individual, entity, and/or device seeking data regarding a particular patient/member or blinded data regarding a characteristic (e.g., illness, treatment, etc) relating to any number of patients/members. The requester 114 receives the encrypted data 502 (e.g., encrypted blind data and/or encrypted blind sub-data) from the consolidator or provider 500 (e.g., or data agent). The encrypted data 502 is then decrypted e.g., via decryptor 510. The decryptor 510 may be embodied in software, hardware or a combination thereof. The decryptor 510 may, for example, decrypt the data using a private key, known only to the requester 114, and a unique identifier assigned to the transaction.

Following decryption, the blind data 520 may be displayed via a display 514. In some instances (i.e., member data requests), the blind data 520 may also be re-associated with a particular member. Blind data 520 having the patient identifying information restored may be referred to as a virtual medical record. It should be noted however, that generally the blind data 520 may not be re-associated with a particular member unless the requester previously possessed the identity of the member. For example, an authorized provider may have the identity of a member and request data related to that member. However, a requester that is a researcher for example would have no means to re-associate blind data with a particular member.

As shown, the local member record 512 (or local data 522 there from) identifying the particular member may also be simultaneously displayed with the virtual medical record. Such combination or concurrent display of a local member record with one or more virtual medical records may be referred to as a provider medical record. In some embodiments, the requester 114 (e.g., a provider and/or doctor) may further select data from the virtual medical record to include in the local member record 512. Upon combination or concurrent display a doctor may select (e.g., via a user interface) at least a portion of the virtual medical record to add to or permanently store with the local member record 512. For example, the doctor may use a check-box scheme to select the data she wishes to validate (e.g., data determined to be credible and useful) and/or to permanently add to the local member record 512. Therefore, the requester's local member record 512 will generally include all data generated by the requester 114 and may also include some data validated by the requester 114. However, some embodiments of the system may include means by which to limit a requester from storing all of the data from a virtual record (unless the requestor is also the patient's consolidator). For example, a requestor's ability to store the data may be limited to a select group of data related to the condition being treated. As one of ordinary skill in the art will understand, such limitations may be preferred as a means to limit and/or control the replication of the sensitive data and the instances of a complete sensitive record.

Figure 6:
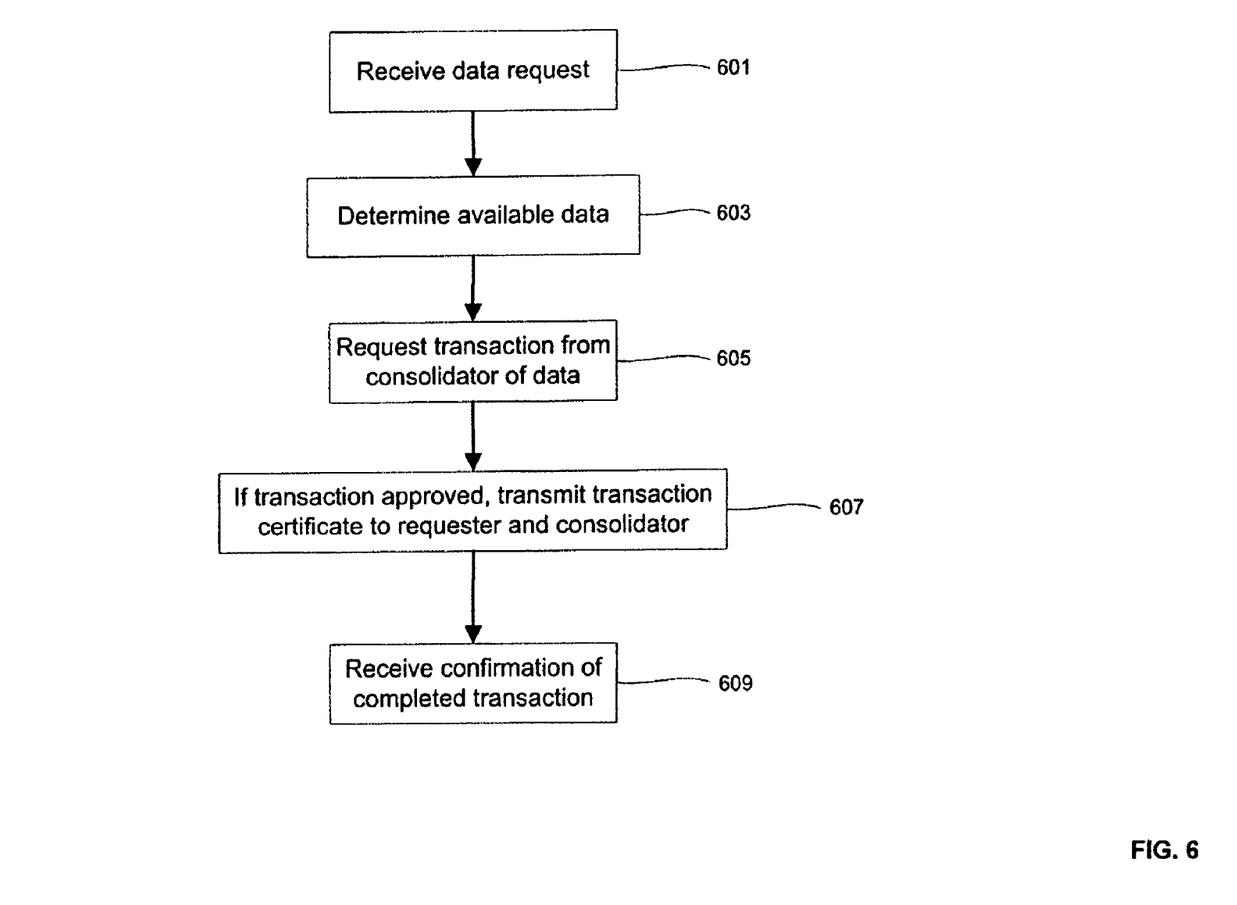
FIG. 6 is a method of processing a sensitive data transaction employable by the system shown in FIGS. 1-5.

FIG. 6 shows a method of processing a sensitive data transaction employable by the systems shown in FIGS. 1 and 4. Step 601 of the method includes receiving a data request, e.g., at a transaction processor. The data request may come from any requester, provider, and/or researcher. The receiver of the data request (e.g., transaction processor) may then query any number of databases to determine the location or locations of the data (step 603). For example, the transaction processor may query a database of particular member identifiers (e.g., in response to a request specific member data) or a database of particular data types (e.g., in response to a blind research request). Next, a transaction may be requested from the one or more consolidators of the requested data (step 605). If the transaction request is approved, a transaction certificate may be transmitted to each of the requester and consolidator (step 607). Following direct communications between the requester and consolidator, the transaction processor may receive confirmation of completed transaction from either or both of the requester and consolidator (step 609).

Figure 7:
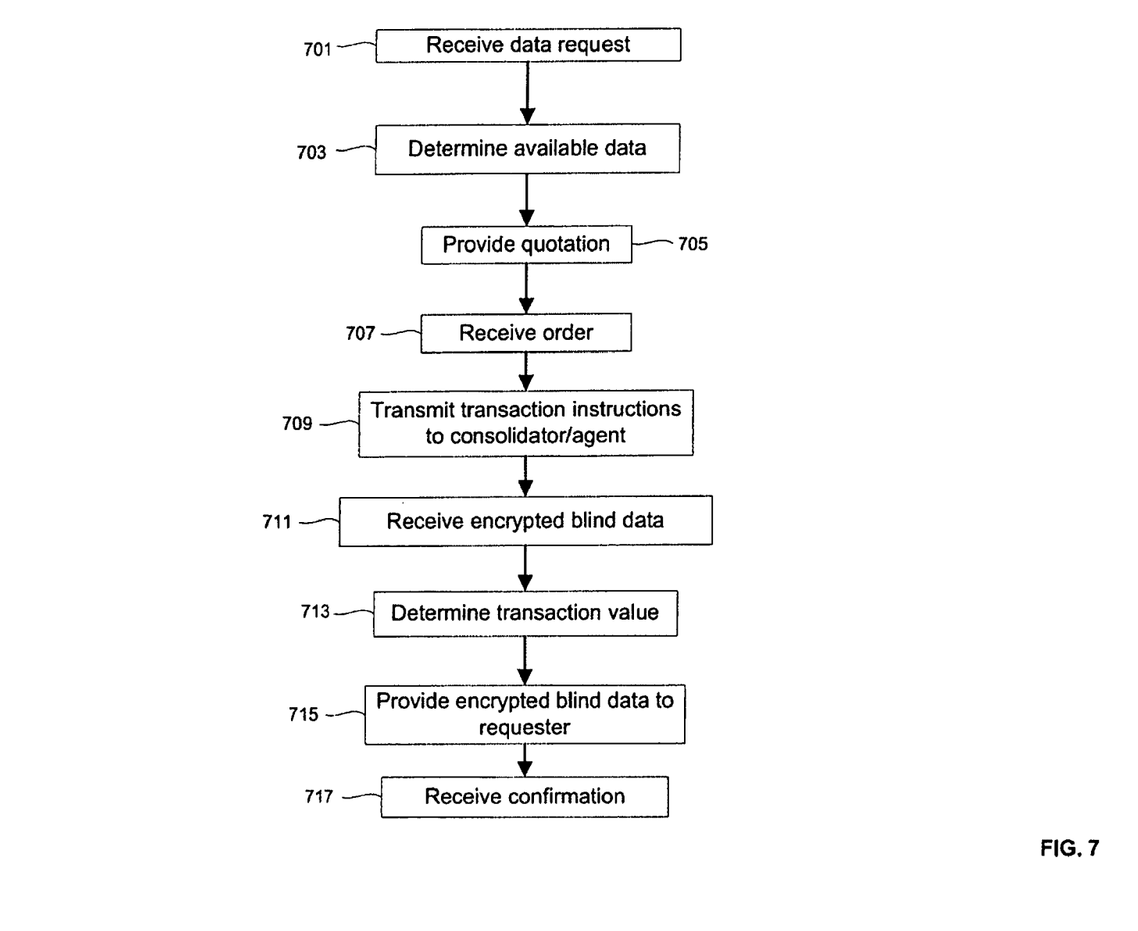
FIG. 7 is another method of processing a sensitive data transaction employable by the system shown in FIGS. 1-5.

FIG. 7 shows another method of processing a sensitive data transaction employable by the systems shown in FIGS. 1 and 4. The method includes a first step of receiving a data request (step 701). The available data may then be determined, e.g., by the transaction processor (step 703). For example, the types, quantity and locations of data responsive to the request may be determined. The transaction processor may then provide a quotation to the requester (step 705). If the quotation is approved (or modified), the transaction processor may receive an order (step 707). In step 709, a transaction request or instructions may be transmitted to a data agent and/or consolidator having access to the requested data. The data agent and/or consolidator may assemble the data and/or provide the transaction request to any number of other data agents and consolidators. The transaction processor may next receive encrypted blind data and optionally a transaction report (step 711).

In step 713, the transaction processor may determine a value of the transaction. As described above, this may be done via a transaction report and/or a meter. The transaction processor may further provide the encrypted blind data to the requester (e.g., and the transaction value or invoice) and subsequently receive a confirmation (steps 715-717).

Figure 8:
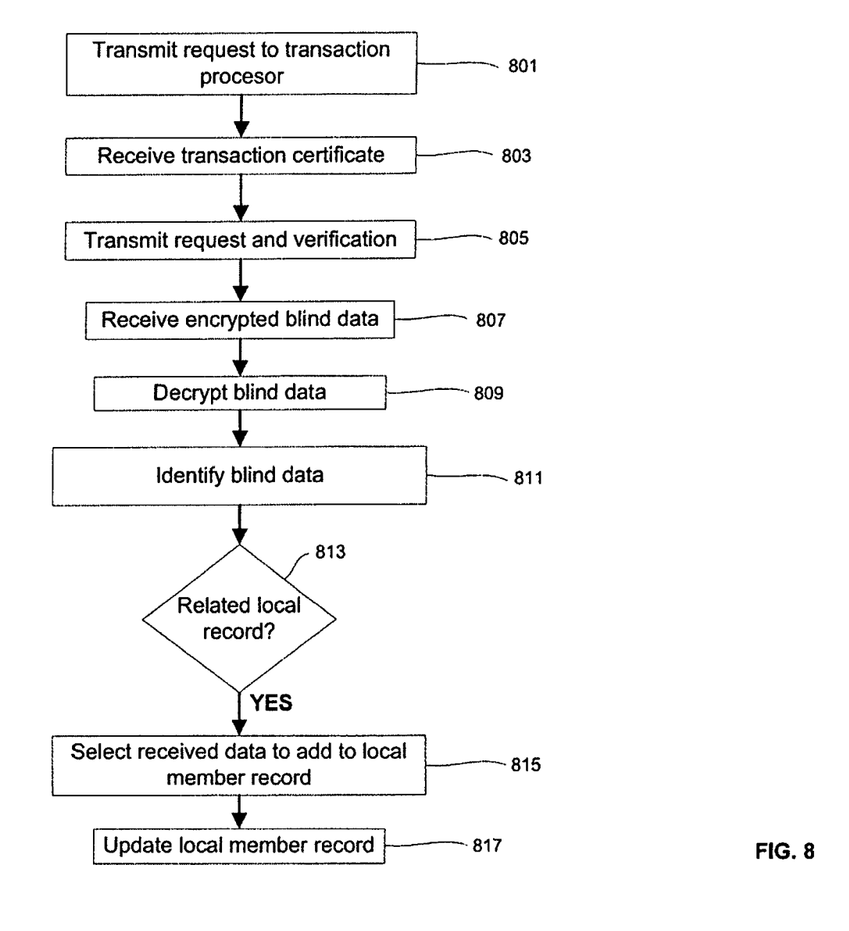
FIG. 8 is a method of requesting sensitive data employable by the system shown in FIGS. 1-5.

FIG. 8 shows a method of requesting data and updating a local data record according to the present invention. The method may include a first step 801 of transmitting a request to a transaction processor. As detailed above, the request may originate from any requester such as a provider and/or a researcher. Following the transaction processor consulting with one or more consolidators, the requester may receive a transaction certificate (step 803). The requester may then transmit a request and verification directly to the consolidator (step 805). Next, the requester may receive encrypted blind data from the consolidator and further decrypt the encrypted blind data (step 807-809). In the instances where the requester has requested data pertaining to a particular member, the requester may then identify the blind data and/or re-associate a member identifier with the blind data (step 811). Further, if a local member record exists for the member, the requester may select a portion or all of the received data to add to the local record (step 813-815). Finally, the local member record may be updated accordingly (step 817).

Advantages of the present invention include the provision of a global repository of sensitive data accessible only by those having authorization. The present invention is particularly useful for maintaining medical histories and making such medical histories accessible for treatment purposes. Advantages of the present invention further include the provision of a system for conducting research queries of sensitive data and allowing access to an extensive network of blind medical data.

Although the invention has been described with reference to a particular arrangement of parts, features and the like, these are not intended to exhaust all possible arrangements or features, and indeed many modifications and variations will be ascertainable to those of skill in the art.

What is claimed is:

1. A system for transferring and updating sensitive data, comprising:
    a plurality of sensitive data records stored at two or more providers, at least some of the data records including data identifying one or more particular members;
    one or more consolidators having access to each of the plurality of sensitive data records via the two or more providers;
    a transaction processor for processing a transfer of data from one or more of the sensitive data records;
    software executing on said transaction processor for receiving a data request from a requester;
    software executing on said transaction processor for determining at least one consolidator having access to the requested data; and
    software executing on said transaction processor for introducing the requester to the at least one consolidator,
    wherein the requestor receives at least a portion of the requested data, the portion excluding data identifying the one or more particular members.

2. The system according to claim 1, wherein the consolidator transmits a subrequest for data to at least one particular data provider, and wherein the at least one data provider transmits at least a portion of the requested data, omitting data identifying the particular member, to the requester.

3. The system according to claim 1, wherein the requestor receives the at least a portion of the requested data from the consolidator.

4. The system according to claim 3, further comprising:
    software executing on the at least one consolidator for omitting identifying data from requested data.

5. The system according to claim 1, wherein the plurality of sensitive data records include at least some first data fields including anonymous data and at least some second data fields including non-disclosable data identifying at least one particular member.

6. The system according to claim 5, wherein the requested data, omitting data identifying the particular member, includes data from the second fields.

7. The system according to claim 1, wherein each sensitive data record includes data corresponding to a particular member.

8. The system according to claim 1, wherein the data request includes a request for medical records of a particular member, wherein the member is a patient.

9. The system according to claim 1, wherein the requestor is a health care provider.

10. The system according to claim 1, further comprising:
    a rules database including one or more rules pertaining to the access of the sensitive data records; and
    wherein the portion of the requested data provided to the request is determined at least in part by the one or more rules.

11. The system according to claim 1, further comprising:
    a directory comprising a plurality of member ID's indicative of individuals having sensitive data records accessible by the system, said directory further comprising a location of at least one consolidator or data provider having a sensitive data record associated with a member ID.

12. A system for transferring and updating sensitive data, comprising:
    at least one data agent having access to a plurality of sensitive data records stored at two or more providers;
    a transaction processor for processing a transfer of data from one or more of the sensitive data records;
    software executing on said transaction processor for receiving a data request from a requester;
    software executing on said transaction processor for determining the at least one data agent having access to the data;
    software executing on said transaction processor for transmitting a transaction request to the at least one data agent, wherein the at least one data agent transmits a subrequest for data to at least one of the data providers, and wherein the at least one data provider transmits at least a portion of the requested data, omitting identifying data; and
    software executing on said transaction processor for receiving blinded data responsive to the data request from the at least one data agent and transmitting the blinded data to the requester.

13. The system according to claim 12, further comprising:
    software executing on said transaction processor for determining a cost of the transaction.

14. The system according to claim 12, wherein the data transferred by said transaction processor consists of disclosable data.

15. The system according to claim 12, wherein each of the plurality of sensitive data records include data corresponding to a particular patient.

16. The system according to claim 15, wherein the blinded data excludes data identifying a particular patient.

17. The system according to claim 12, further comprising:
    software executing on said transaction processor for encrypting the blinded data.

18. The system according to claim 12, further comprising:
    a rules database including one or more rules pertaining to the access of the sensitive data records; and
    wherein the blinded data transmitted to the requestor is determined at least in part by the one or more rules.

19. A method of processing a transfer of sensitive data, comprising the steps of:
    receiving a data request from a requester;
    querying a database of record identifiers to determine at least one consolidator having access to the requested data;
    transmitting a transaction request to a consolidator, wherein the consolidator determines at least one data provider having the requested data;
    transmitting a subrequest to the at least one data provider;
    transmitting a transaction certificate to the requester and the consolidator if the transaction is approved by the at least one consolidator;
    transmitting the request and certificate information from the requester to the consolidator;
    blinding data responsive to the data request to remove data identifiable to any particular individual; and
    transmitting the blinded data to the requestor.

20. The method according to claim 19, further comprising the step of:
    encrypting the blinded requested data.

21. The method according to claim 19, further comprising the step of:
    receiving a confirmation upon completion of the transaction.

22. The method according to claim 19, further comprising the step of:
    reassociating an identity of a particular individual with the requested data.

23. The method according to claim 19, wherein the data request is a request for a medical record of a particular patient.

24. The method according to claim 19, wherein the data request is a request for medical data related to a particular illness.

25. The method according to claim 24, wherein the blinded data includes data related to a plurality of anonymous individuals.

26. The method according to claim 19, further comprising the step of:
querying one or more rules pertaining to the access of the sensitive data records to determine the blinded data transmitted to the requestor.

27. A method of transferring and updating sensitive data, comprising the steps of:
receiving a data request from a requester;
querying a database of record identifiers to determine one or more data agents have access to the requested data;
providing a quotation to the requester;
receiving an order from the requester;
transmitting a transaction request to the one or more data agents;
accessing the requested data from two or more data providers accessible to the one or more data agents;
receiving blinded data responsive to the data request from at least one of the data agents and the data providers;
determining a cost of the transaction; and
transmitting the blinded data to the requester.

28. The method according to claim 27, wherein the blinded data consists of data excluding identifying information.

29. The method according to claim 27, further comprising the step of:
encrypting the blinded data.

30. The method according to claim 27, wherein the data request is a request for medical data related to a particular illness.

31. The method according to claim 27, wherein the transmitted blinded data includes data related to a plurality of anonymous individuals.

32. The method according to claim 27, further comprising the step of:
querying one or more rules pertaining to the access of the sensitive data records to determine the blinded data transmitted to the requestor.

* * * * *